United States Patent [19]

Fox et al.

[11] 3,980,580

[45] Sept. 14, 1976

[54] OXYGEN CARRIER COMPOSITION

[75] Inventors: Dale B. Fox; Talmage D. McMinn, Jr., both of St. Louis; Rodney D. Beckham, Bridgeton; Phillip D. Montgomery, Creve Coeur, all of Mo.

[73] Assignee: Monsanto Company, St. Louis, Mo.

[22] Filed: Jan. 2, 1974

[21] Appl. No.: 430,282

[52] U.S. Cl. .................................. 252/186; 149/40; 252/463; 423/600
[51] Int. Cl.² .................... B01J 21/02; B01J 21/10; B01J 23/14
[58] Field of Search ............ 252/186, 463; 423/600; 260/668 D; 149/119, 40

[56] References Cited
UNITED STATES PATENTS

| | | | |
|---|---|---|---|
| 3,329,727 | 7/1967 | Louvar | 252/463 |
| 3,435,089 | 3/1969 | Moore et al. | 252/463 |
| 3,436,358 | 4/1969 | Thygesen | 252/463 |
| 3,438,724 | 4/1969 | Hartford et al. | 423/600 |
| 3,498,927 | 3/1970 | Stiles | 252/463 |
| 3,791,992 | 4/1974 | Feldwick | 252/463 |

*Primary Examiner*—Benjamin R. Padgett
*Assistant Examiner*—Irwin Gluck
*Attorney, Agent, or Firm*—Paul L. Passley

[57] ABSTRACT

An oxygen carrier composition based on the metals lead, magnesium and aluminum and a vapor phase process for dehydrocoupling toluene and/or toluene derivatives to form stilbene and/or stilbene derivatives and for demethylating toluene and/or toluene derivatives to form benzene and/or benzene derivatives.

7 Claims, No Drawings

OXYGEN CARRIER COMPOSITION

BACKGROUND OF THE INVENTION

This invention relates to a composition containing oxygen, lead, magnesium and aluminum and to the use of such composition in the oxidative synthesis of stilbene from toluene and the demethylation of toluene to produce benzene.

Stilbene, because of its unsaturated character, is very reactive and may be employed in various ogranic syntheses. Derivatives of stilbene are useful in the production of products which may be used in the manufacture of dyes, paints and resins. It is also useful in optical brighteners, in pharmaceuticals and as an organic intermediate.

Stilbene has been synthesized by dehydrogenation of bibenzyl; by dehydrogenation of 1,2-bis(3-cyclo-hexe-1-yl) ethylene (U.S. Pat. No. 3,387,050); and by reacting a benzyl mercaptan with a sulfactive catalyst, for example, molybdenum disulfide and copper sulfide (U.S. Pat. No. 2,645,671). Stilbene and halostilbenes have been synthesized by the iodative dehydrocoupling of toluene and halogen substituted toluenes with elemental iodine and molten lithium iodide at toluene conversions of 10–30% (U.S. Pat. No. 3,409,680).

Dehydrocoupling of toluene by the reaction with lead oxide to form stilbene has been reported by Behr and Van Dorp, Chem. Ber. 6, 753 (1873) and Lorenz, Chem. Ber. 7, 1096 (1874). In this reported work, stilbene is obtained by conveying toluene over lead oxide maintained at or about at a dark red glow. A more recent disclosure of the toluene lead oxide reaction is given in U.S. Pat. No. 3,494,956. In Example 9 of this patent, it is reported that a mixture of toluene and oxygen passed over heated lead oxide produces bibenzyl.

Benzene is a valuable hydrocarbon having many uses. A major use today is in the production of styrene by ethylene alkylation to form ethylbenzene followed by dehydrogenation to form styrene. Styrene finds use as a monomer in the polymer field.

SUMMARY

This invention is directed to an oxygen carrier composition wherein the oxygen is associated with lead, magnesium and aluminum as oxides or complexes or mixtures thereof and to the use of such composition as the oxygen supply in the oxidative conversion of toluene to stilbene and benzene.

Accordingly, typical objects of this invention are to provide (1) an improved oxygen carrier composition useful as the oxygen supply in oxidative reactions, (2) an improved method of making a composition of oxides of and/or oxygen complexes of lead, magnesium and aluminum, (3) improved vapor phase processes for the production of stilbenes and benzenes, (5) an improved vapor phase dehydrocoupling process for converting toluene and its derivatives to stilbene and its derivatives, and (6) an improved vapor phase process for demethylating toluene to benzene.

Other objects, advantages and aspects of this invention will become apparent to those skilled in the art upon further study of this disclosure and the appended claims.

In accordance with this invention in a first aspect a composition is provided which contains oxygen in such a manner that it is capable of releasing stoichiometric quantities of oxygen under oxidative reaction conditions. The oxygen in the composition is associated with the metals lead, magnesium and aluminum as individual metal oxides, as oxygen complexes of at least two of the metals or as lead oxide in combination with magnesium aluminate. The composition can be represented by the empirical formula $Pb_aMg_bAl_cO_d$ wherein $a$ is a number from 0.005 to 1.0, $b$ is a number from 0.5 to 1.5, $c$ is a number from 0.5 to 5.0, and $d$ is a number which satisfies the oxidation states of the Pb, Mg and Al and their quantities contained in the composition. The materials of the composition can be expressed as a loading of PbO on $MgAl_2O_4$. The PbO will generally comprise 10 to 50 weight percent of the total composition. A suitable composition is $Pb_{0.12}Mg_1Al_2O_{4.12}$.

The composition can be prepared in any known manner. A satisfactory method is the coprecipitation of salts of the Pb, Mg and Al. Suitable salts of the metals which can be used are nitrates, formates and acetates. Precipitation of the salts is caused by the addition of a base, such as ammonium hydroxide. After precipitation and washing of the filter cake to remove ammonium nitrates, formates, etc., the filter cake is calcined to form the oxides and/or oxygen complexes. The time and temperature of calcination can vary over wide ranges and be used to obtain desired surface areas and pore size distribution. Generally, the calcination will be conducted at a temperature of from 900° to 1400°C and for a time of from 0.5 to 24 hours. The pH employed for precipitation of the metal salts can vary over a wide range. However, this invention finds that the pH can be used to control or to produce compositions having particular selectivity for certain oxidative reactions. In this regard, if the pH of the precipitation of the salts is about 6 to 8, preferably about 7 the composition is most effective in demethylating toluene to form benzene and if the pH of the precipitation of the salts is about 8 to 11, preferably about 8.7 the composition is most effective for dehydrocoupling toluene to form stilbene. Another method for forming the composition is by impregnating alumina with magnesium salts followed by drying and high temperature calcination and then impregnating the calcined magnesia-alumina material with lead salts followed by drying and high temperature calcination. Still another satisfactory method of forming the composition is by the impregnation of spinel ($Mg Al_2 O_4$) with lead salts followed by drying and high temperature calcination. The spinel can be synthesized from various magnesium and aluminum compounds and by several known procedures. A useful method for formation of the spinel is by precipitation of salts, such as nitrates, formates and acetates of magnesium and aluminum. The precipitation is generally conducted at a temperature in the range of 30° to 85°C. After precipitation of the metal salts the washing of the filter cake can be regulated to effect the surface area of the spinel. If the filter cake is washed to remove all of the ammonium nitrates, formates, etc., the surface area will generally be less than 6 m²/gm, but by reducing the washing of the filter cake the surface area of the spinel prepared can be regulated within the 8–60 m²/gm. range. Calcination temperatures used will generally be within the range of 900° to 1400°C.

In accordance with another aspect of this invention, toluene and toluene derivatives are dehydrocoupled in a one step process to stilbene and stilbene derivatives or demethylated in a one step process to benzene and benzene derivatives in the vapor phase in the presence of the above described oxygen carrier composition. The dehydrocoupling reaction is conducted at a temperature of from 500° to 650°C, preferably from 540° to 580°C and the demethylation reaction is conducted at a temperature of from 500° to 650°C, preferably from 575° to 625°C. Both reactions are carried out in the absence of added free oxygen and utilize only that oxygen supplied by the above described oxygen carrier composition. The dehydrocoupling reaction will suitably be conducted at a toluene conversion level of 20 to 55 percent and the demethylation reaction at a toluene conversion level of 30 to 80 percent. Such levels of conversion tends to give the better selectivity for the respective reactions.

Pressures other than atmospheric may be employed in the process of this invention, however, it will generally be preferred to conduct the reaction at or near atmospheric pressure.

The reaction time for the toluene in contact with the oxygen carrier composition in this invention may be selected from a broad operable range which may vary from about 0.1 to about 60 seconds. The reaction time may be defined as the length of time in seconds which the reactant gases measured under reaction conditions are in contact in the reactor. Preferably, the reaction time will be within the range of 0.5 to 20 seconds.

The reaction may advantageously be conducted in the presence of diluents to enhance selectivity toward the desired product. Steam is a useful diluent. The diluent when used will be present in a ratio of 0.1 to 10, preferably 0.5 to 1.5, parts of diluent per part of hydrocarbon.

The reactor employed may be brought to the desired reactor temperature before or after introduction of the vaporized reactants. Preferably, the feed materials are preheated, vaporized and generally thoroughly mixed prior to introducing them to the reactor.

The oxygen carrier composition of this invention can be employed in a fixed bed or fluidized bed reactor system. Accordingly, the processes for utilizing the oxygen carrier composition can be conducted as fixed bed or fluidized bed processes.

The products of the reaction may be recovered from the effluent gas by any appropriate method and means known to the art and further elucidation here will be unnecessary duplication of the art. The unreacted toluene and/or toluene derivatives are recovered and recirculated to the reactor.

DESCRIPTION OF PREFERRED EMBODIMENTS

The following Examples are given as illustrative of the invention and, as such, specifics set forth are not intended to be unduly considered limitations upon the scope of the invention.

The reactor employed in the following Examples I–III is a ½ inch diameter stainless steel tube 1 foot long equipped at the upper end with inlet means for introducing the reactant and at the bottom end with outlet means for collecting the reaction effluent or for introducing it into a gas chromatograph for analysis.

EXAMPLE I

A magnesia-alumina supported PbO catalyst is prepared by melting 1180.6 grams of $Mg(NO_3)_2 \cdot 6H_2O$ and mixing the melt with 470 grams of 50–150 mesh alumina having a surface area of 250 $m^2$/gm. This mixture is calcined at 500°C for 5 hours, screened to remove dust, and calcined at 1100–1200°C for 12 hours. After cooling this material is screened to provide hard particles (40–270 mesh) of magnesium aluminate spinel having a surface area of 4.3 $m^2$/gm. These particles are impregnated with sufficient $Pb(NO_3)_2$ to provide a loading of 20% PbO, dried and calcined at 500°C for 4 hours.

Steam and toluene in a 2:1 mole ratio are fed at a temperature of 600°C to the reactor heated with a radiant furnace containing 19.7 ml of the supported PbO at such a rate to give a 1 second residence time of the toluene in the reactor. After the reaction has proceeded for 1 minute, analysis of the effluent indicates 41.2% of the toluene is reacted of which 67.1% is converted to stilbene, 1.8% to bibenzyl, 26.8% to benzene and 1.4% to $CO_2$.

EXAMPLE II

A magnesia-alumina supported PbO catalyst is prepared by forming a solution of 1581 grams of $Al(NO_3)_3 \cdot 9H_2O$ and 541 grams of $Mg(NO_3)_2 \cdot 6H_2O$ in 2 liters of water. The pH of the solution is adjusted to 9.0 by adding ammonium hydroxide to cause precipitation of magnesium and aluminum hydroxides. After filtering, the precipitate is washed with water, dried in vacuo for 16 hours at 120°C, crushed and screened to 20–140 mesh, redried in vacuo for 48 hours at 180°C and calcined at 1200°C for 3.5 hours. After cooling, the calcined precipitate is very hard, has a surface area of 3$m^2$/gm. and an XRD analysis of 80–98% magnesium aluminate spinel. The calcined precipitate is stirred into a water solution of $Pb(NO_3)_2$ containing sufficient $Pb(NO_3)_2$ to give a loading of 10% PbO. After evaporating the water in vacuo, the mixture is calcined at 600°C for 3.5 hours. The supported catalyst has a surface area of 1.6$m^2$/gm.

Example I is repeated except that the temperature is 610°C and the residence time of the toluene is 2 seconds. After 1 minute of operation, analysis indicates 30.7% of the toluene is reacted of which 64.4% is converted to stilbene, 6.8% to bibenzyl and 24.8% to benzene.

EXAMPLE III

An oxygen carrier composition within the invention is prepared by adding 48.7 grams of $MgCl_2 \cdot 6H_2O$ dissolved in 60 ml of hot water to 50 grams (70 ml) of a commercial alumina ($Al_2O_3$). After drying the mixture in vacuo and screening to remove dust (less than -270 mesh), the mixture is calcined at 1100°C for 28 hours. After cooling, the calcined material is screened and 51 grams of 40–270 mesh solid having a surface area of 2.5 $m^2$/gm. is collected. The collected material is impregnated with sufficient $Pb(NO_3)_2$ — about 18.9 gm to provide a loading of 20% PbO — dissolved in 100 ml water which is then dried and calcined at 600°C for 4 hours.

Water and toluene in a 2:1 mole ratio is fed at a temperature of 600°C to the reactor heated with a radiant furnace containing 61.8 grams of the above prepared oxygen carrier material at such a rate to give a 2 seconds residence of toluene in the reactor. After the reaction has proceeded for one minute, analysis of the effluent indicates 36.1% of the toluene is reacted of which 65.7 is converted to stilbene, 3.1% to bibenzyl and 27.3% to benzene.

EXAMPLE IV

A magnesium aluminate is prepared by forming an aqueous solution of $Al(NO_3)_3 \cdot 9H_2O$ and $Mg(NO_3)_2 \cdot 6H_2O$ having a molar ratio of Al/Mg of 2 to 1. Into the solution maintained at 80°C is stirred a water solution of $NH_4OH$ until the pH is between 8 to 9.5. The precipitate is collected on a filter and washed thoroughly with water at a temperature of 80°C. The thus washed precipate is dried, ground and then calcined at about 1200°C for 6 hours. The calcined material by XRD analysis contains 93–99% $MgAL_2O_4$ and has a surface area of 52.8 m²/gm.

It will be obvious to persons skilled in the art that various modifications may be made in the process as described in this application. Accordingly, it is intended that all such modifications which reasonably fall within the scope of the appended claims are included herein.

What is claimed is:

1. An oxygen carrier composition which comprises oxygen and the metals lead, magnesium and aluminum represented by the empirical formula $$Pb_a Mg_b Al_c O_d$$

where $a$ is a number from 0.005 to 1.0, $b$ is a number from 0.5 to 1.5. $c$ is a number from 0.5 to 5.0 and $d$ is a number which satisfies the oxidation states of the metals and their quantities contained in the composition.

2. The composition of claim 1 wherein the composition of oxygen and the metals has the empirical formula $$Pb_a Mg_b Al_c O_d$$

wherein $a$ is 0.12, $b$ is 1, $c$ is 2 and $d$ is 4.12.

3. The composition of claim 1 wherein the composition is PbO supported on $MgAl_2O_4$.

4. The composition of claim 3 wherein the loading of PbO on $MgAl_2O_4$ is 1.0 to 50 weight percent of the total composition.

5. The process of preparing an oxygen carrier composition based on oxygen and the metals lead, magnesium and aluminum which comprises forming a solution of salts of the metals, adjusting the pH of the solution to from 7.0 to 11.0 by the addition of a base to cause precipitation of the metals, recovering the precipitate, washing the recovered precipitate to remove the formed basic salts, and drying and calcining the washed precipitate to form the composition of oxygen and the metals.

6. The process of claim 5 wherein the solution is aqueous, the metal salts are nitrates, the base is ammonium hydroxide, the pH is adjusted to 7–10, and the calcination is conducted at a temperature of 900° to 1400°C for from 0.5 to 24 hours.

7. The process of claim 5 wherein the ratio of salts of Mg:Al is from 2:1 to 1:5 and of Pb:Mg is from 0.005:1 to 2:1.

* * * * *